United States Patent
Izumimoto et al.

(10) Patent No.: US 8,946,267 B2
(45) Date of Patent: Feb. 3, 2015

(54) THERAPEUTIC AGENT OR PROPHYLACTIC AGENT FOR NEUROPATHIC PAIN

(75) Inventors: Naoki Izumimoto, Kamakura (JP); Hidenori Mochizuki, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/813,242

(22) PCT Filed: Jul. 29, 2011

(86) PCT No.: PCT/JP2011/067431
§ 371 (c)(1),
(2), (4) Date: Jan. 30, 2013

(87) PCT Pub. No.: WO2012/015027
PCT Pub. Date: Feb. 2, 2012

(65) Prior Publication Data
US 2013/0131120 A1    May 23, 2013

(30) Foreign Application Priority Data

Jul. 30, 2010   (JP) ................................. 2010-171384

(51) Int. Cl.
| | | |
|---|---|---|
| A01N 43/40 | (2006.01) | |
| A61K 31/44 | (2006.01) | |
| A61K 31/415 | (2006.01) | |
| A61K 31/197 | (2006.01) | |
| A61K 45/06 | (2006.01) | |
| A61K 31/421 | (2006.01) | |
| A61K 31/426 | (2006.01) | |
| A61K 31/4439 | (2006.01) | |
| A61K 31/195 | (2006.01) | |
| A61K 31/422 | (2006.01) | |
| A61K 31/427 | (2006.01) | |

(52) U.S. Cl.
CPC ............. *A61K 31/415* (2013.01); *A61K 31/197* (2013.01); *A61K 45/06* (2013.01); *A61K 31/421* (2013.01); *A61K 31/426* (2013.01); *A61K 31/4439* (2013.01); *A61K 31/195* (2013.01); *A61K 31/422* (2013.01); *A61K 31/427* (2013.01)
USPC ............ 514/341; 514/365; 514/374; 514/406

(58) Field of Classification Search
CPC ............ A61K 2300/00; A61K 31/195; A61K 31/422; A61K 31/427; A61K 31/4439; A61K 31/197; A61K 31/415; A61K 31/421; A61K 31/426; A61K 45/06
USPC ................... 514/341, 365, 374, 406
See application file for complete search history.

(56) References Cited

U.S. PATENT DOCUMENTS

| | | |
|---|---|---|
| 4,024,175 A | 5/1977 | Satzinger et al. |
| 6,436,966 B1 | 8/2002 | Ohkawa et al. |
| 8,247,569 B2 * | 8/2012 | Morita et al. ............... 546/275.4 |
| 2013/0190503 A1 | 7/2013 | Yoshida et al. |

FOREIGN PATENT DOCUMENTS

| | | |
|---|---|---|
| JP | 51-88940 A | 8/1976 |
| JP | 2007-508288 A | 9/1995 |
| JP | 11-193281 | 7/1999 |
| JP | 2004-536873 | 12/2004 |
| JP | 2005-60311 | 3/2005 |
| WO | 93/23383 | 11/1993 |
| WO | 01/13904 | 3/2001 |
| WO | 01/24792 | 4/2001 |
| WO | 2004/016259 | 2/2004 |
| WO | 2005/025675 | 3/2005 |
| WO | 2005/102390 | 11/2005 |
| WO | 2007/090661 | 8/2007 |
| WO | 2008/079720 | 7/2008 |
| WO | 2008/079727 | 7/2008 |
| WO | 2009/021058 | 2/2009 |
| WO | 2010/025931 | 3/2010 |
| WO | 2010/050577 | 5/2010 |

(Continued)

OTHER PUBLICATIONS

Roane et al, J Neuropsychiatry Clin Neurosci 12:1, Winter 2000.*
Grosch, Rheumatology, Jun. 13, 2007.*

(Continued)

*Primary Examiner* — Wu-Cheng Winston Shen
*Assistant Examiner* — Jean Cornet
(74) *Attorney, Agent, or Firm* — DLA Piper LLP (US)

(57) ABSTRACT

A therapeutic agent or a prophylactic agent for neuropathic pain provides a synergistically-enhanced analgesic effect at a dose at which a calcium channel α2δ ligand does not produce any side effects as well as which agent does not produce any new side effects on the central nervous system. The therapeutic agent or a prophylactic agent for neuropathic pain includes as effective ingredients a cyclohexane derivative, represented by the following formula, or a pharmaceutically acceptable salt thereof or a prodrug thereof, and a calcium channel α2δ ligand.

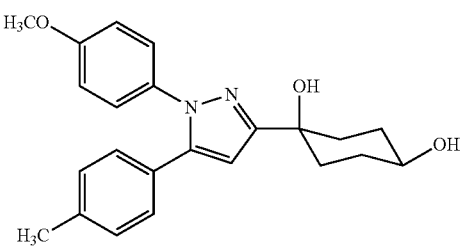

3 Claims, 3 Drawing Sheets

(56) References Cited

FOREIGN PATENT DOCUMENTS

| WO | WO 2010050577 A1 | * | 5/2010 |
| WO | 2011/125836 A1 | | 10/2011 |

OTHER PUBLICATIONS

The Supplementary European Search Report issued on Nov. 8, 2013 in corresponding European Patent Application No. 11812616.8.

D.J. Dooley et al., "Ca2+ channel alpha2delta ligands: novel modulators of neurotransmission," *Trends Pharmacol Sci*, Feb. 2007, vol. 28, p. 75-82, Abstract only.

G. Zaccara et al., "Central nervous system adverse effects of new antiepileptic drugs. A meta-analysis of placebo-controlled studies," *Seizure*, Jul. 2008, vol. 17, p. 405-421, Abstract only.

A.T. Hama et al., "Cannabinoid receptor-mediated antinociception with acetaminophen drug combinations in rats with neuropathic spinal cord injury pain," *Neuropharmacology*, Mar.-Apr. 2010, vol. 58, p. 758-766.

M.M. Curros-Criado et al., "Antinociceptive effects of NCX-701 (nitro-paracetamol) in neuropathic rats: enhancement of antinociception by co-administration with gabapentin," *Br J Pharmacol*, Jul. 23, 2009, vol. 158, p. 601-609.

M. Hanna et al., "Prolonged-release oxycodone enhances the effects of existing gabapentin therapy in painful diabetic neuropathy patients," *Eur J Pain*, Aug. 2008, vol. 12, p. 804-813, Abstract only.

T. Mixcoatl-Zecuatl et al., "Synergistic antiallodynic interaction between gabapentin or carbamazepine and either benfotiamine or cyanocobalamin in neuropathic rats," *Methods Find Exp Clin Pharmacol*, Jul.-Aug. 2008, vol. 30, p. 431-441, Abstract only.

K. Hayashida et al., "Multiplicative interactions to enhance gabapentin to treat neuropathic pain," *Eur J Pharmacol*, Nov. 19, 2008, vol. 598, p. 21-26, Abstract Only.

M.A. Tomić et al., "Analysis of the antinociceptive interactions in two-drug combinations of gabapentin, oxcarbazepine and amitriptyline in streptozotocin-induced diabetic mice," *Eur J Pharmacol*, Feb. 25, 2010, vol. 628, p. 75-82, Abstract only.

Park et al., "The interaction of gabapentin and N6-(2-phenylisopropyl)-adenosine R-(-)isomer (R-PIA) on mechanical allodynia in rats with a spinal nerve ligation," *J Korean Med Sci*, Aug. 2008, vol. 23, p. 678-184, Abstract only.

A. Imai et al., "Synergy between a NR2B receptor antagonist DHQ and 3-methyl-gabapentin in mice with neuropathic pain," *Eur J Pharmacol*, Jul. 7, 2008, vol. 588, p. 244-247, Abstract only.

E.E. Codd et al., "Tramadol and several anticonvulsants synergize in attenuating nerve injury-induced allodynia," *Pain*, Feb. 2008, vol. 134, p. 254-262, Abstract only.

K. Hayashida et al., "Oral gabapentin activates spinal cholinergic circuits to reduce hypersensitivity after peripheral nerve injury and interacts synergistically with oral donepezil," *Anesthesiology*, Jun. 2007, vol. 106, p. 1213-1219, Abstract only.

M. De la O-Arciniega et al., "Anti-nociceptive synergism of morphine and gabapentin in neuropathic pain induced by chronic constriction injury," *Pharmacol Biochem Behav*, May 2009, vol. 92, p. 457-464, Abstract only.

Z. Seltzer et al., "A novel behavioral model of neuropathic pain disorders produced in rats by partial sciatic nerve injury," *Pain*, Nov. 1990, vol. 43, p. 205-218, Abstract only.

A.B. Malmberg et al., "Partial sciatic nerve injury in the mouse as a model of neuropathic pain: behavioral and neuroanatomical correlates," *Pain*, May 1998, vol. 76, p. 215-222.

* cited by examiner

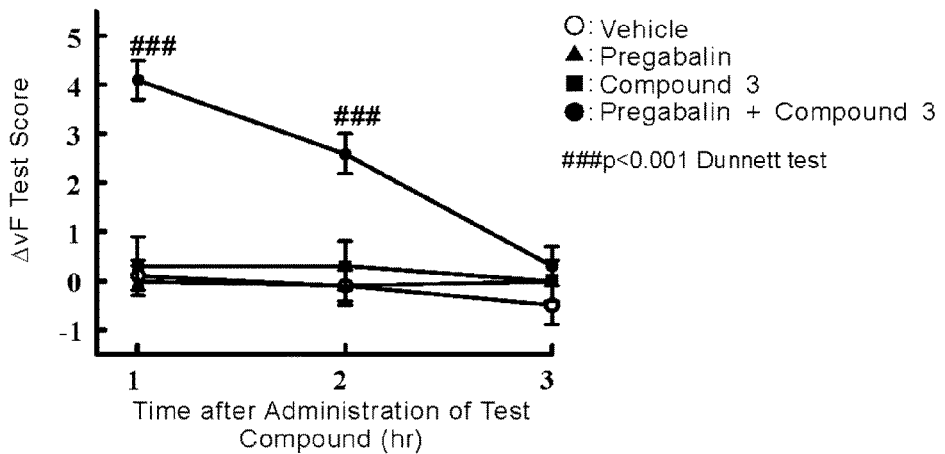
Fig.1
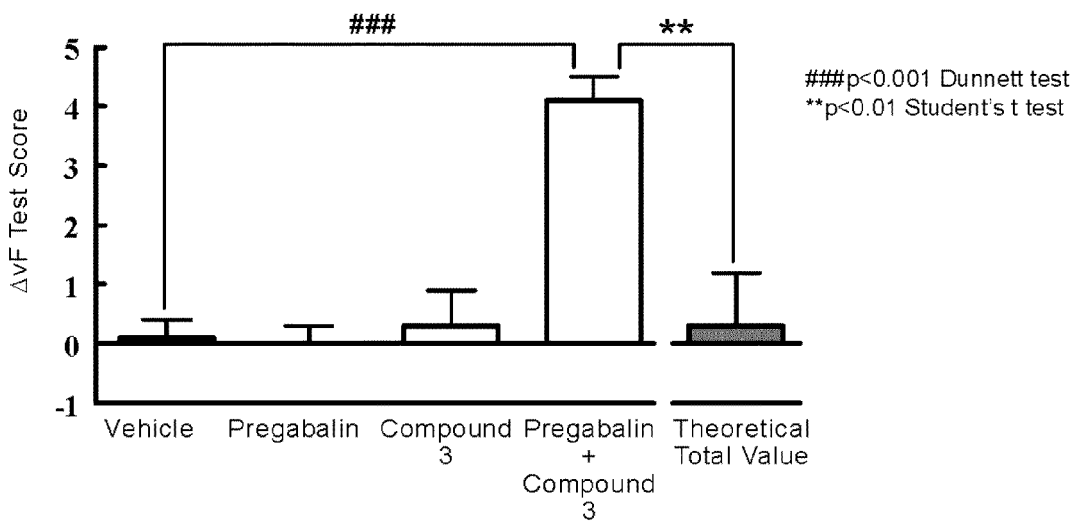
Fig.2-A

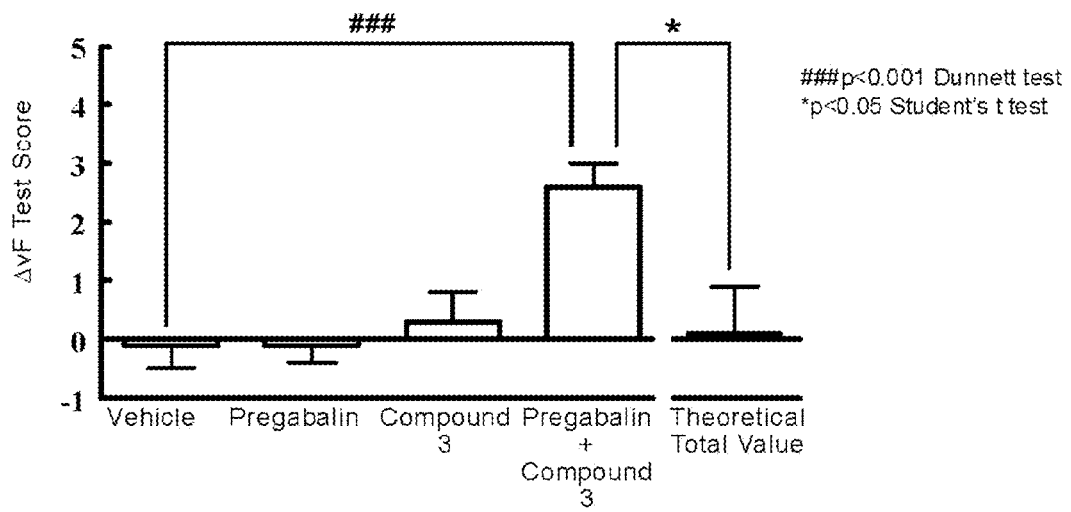
Fig.2-B
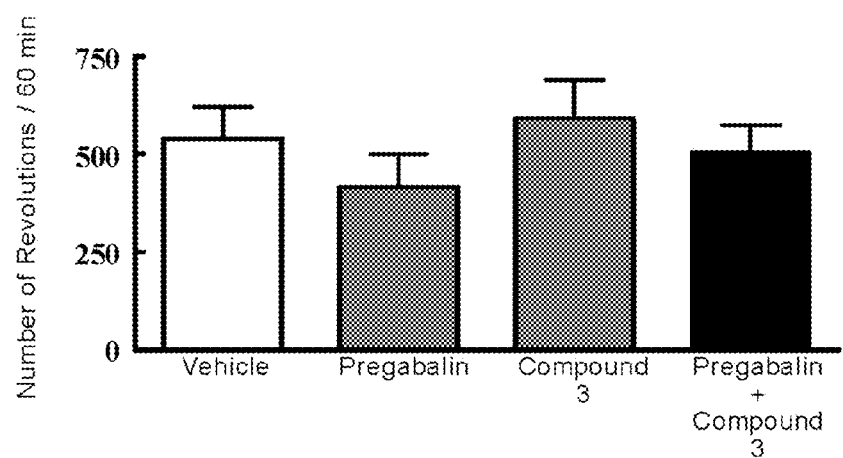
Fig.3

THERAPEUTIC AGENT OR PROPHYLACTIC AGENT FOR NEUROPATHIC PAIN

RELATED APPLICATIONS

This is a §371 of International Application No. PCT/JP2011/067431, with an international filing date of Jul. 29, 2011 (WO 2012/015027 A1, published Feb. 2, 2012), which is based on Japanese Patent Application No. 2010-171384, filed Jul. 30, 2010, the subject matter of which is incorporated herein by reference.

TECHNICAL FIELD

This disclosure relates to a therapeutic agent or a prophylactic agent for neuropathic pain.

BACKGROUND

Neuropathic pain (also referred to as neurogenic pain) means pain caused by a disorder or a disease in the peripheral or central somatosensory nervous system and which results from a direct injury, compression or the like to nerve tissue without any noxious stimuli to a nociceptor.

As a therapeutic drug for neuropathic pain, anticonvulsants, antidepressants and antianxiety agents, as well as antiepileptics including pregabalin and gabapentin, which are calcium channel α2δ ligands, have been used (Dooley et al., Trends Pharmacol Sci, 2007, Vol. 28, p. 75). Among these, pregabalin is a world standard therapeutic drug for neuropathic pain, but it is known that administration of pregabalin frequently causes side effects such as dizziness, somnolence, ataxia, weakness and the like, which are thought to be based on the inhibitory effects on the central nervous system (Zaccara et al., Seizure, 2008, Vol. 17, p. 405).

To reduce the dose of pregabalin or gabapentin, combined use of these calcium channel α2δ ligands with various drugs has been studied in recent years. It has been reported that a synergistic analgesic effect can be obtained by combined use of, for example, a calcium channel α2δ ligand with a phosphodiesterase type 5 inhibitor sildenafil, tadalafil or vardenafil (WO 04/016259) or with other drugs (WO 10/025931, WO 09/021058, WO 08/079727, WO 08/079720, WO 07/090661, WO 05/102390, WO 05/025675, WO 01/024792, WO 01/013904, Tomic et al., Eur J Pharmacol, 2010, Vol. 628, p. 75, Park et al., J Korean Med Sci, 2008, Vol. 23, p. 678, Imai et al., Eur J Pharmacol, 2008, Vol. 588, p. 244, Codd et al., Pain, 2008, Vol. 134, p. 254 and Hayashida et al., Anesthesiology, 2007, Vol. 106, p. 1213), or by combined use of gabapentin with a nonopioid analgesic acetaminophen (Hama et al., Neuropharmacology, 2010, Vol. 58, p. 758) or nitroparacetamol (Curros-Criado et al., Br J Pharmacol, 2009, Vol. 158, p. 601), or with an opioid analgesic oxycodone (Hanna et al., Eur J Pain, 2008, Vol. 12, p. 804) or morphine (De la O-Arciniega et al., Pharmacol Biochem Behav, 2009, Vol. 92, p. 457), or with a vitamin B1 derivative benfotiamine (Mixcoatl-Zecuatl et al., Methods Find Exp Clin Pharmacol, 2008, Vol. 30, p. 431) or vitamin B12 cyanocobalamin (Mixcoatl-Zecuatl et al.). Furthermore, it has been also reported that a synergistic analgesic effect can be obtained by combined use of three drugs, gabapentin, donepezil (cholinesterase inhibitor) and duloxetine (serotonin and noradrenaline reuptake inhibitor) (Hayashida et al., Eur J Pharmacol, 2008, Vol. 598, p. 21).

However, in the combination therapy with a calcium channel α2δ ligand, because such therapy is designed to reduce side effects of the calcium channel α2δ ligand per se, there are at present cases where an analgesic effect is not sufficiently exhibited due to the reduced dosage of the calcium channel α2δ ligand, and cases where new side effects occur due to the increased dosage of the drug used in combination therewith. For example, in the combined use of gabapentin and morphine, it has been reported that impairment in motor coordination occurs at a dosage sufficient to obtain the synergistic analgesic effect (De la O-Arciniega et al., Pharmacol Biochem Behav, 2009, Vol. 92, p. 457). Therefore, it has been thought that, even in the case of using any other drug in combination therewith, it is difficult to avoid the occurrence of side effects on the central nervous system while obtaining the synergistic analgesic effect.

Accordingly, it could be helpful to provide a therapeutic agent or a prophylactic agent for neuropathic pain, by which a synergistically-enhanced analgesic effect is obtained at a dosage at which a calcium channel α2δ ligand does not produce any side effects as well as which agent does not produce any new side effects on the central nervous system.

SUMMARY

We discovered that, when a calcium channel α2δ ligand is used in combination with a cyclohexane derivative which exhibits an excellent analgesic effect against neuropathic pain, the analgesic effect against neuropathic pain is synergistically enhanced without exacerbating side effects of the calcium channel α2δ ligand on the central nervous system.

That is, we provide a therapeutic agent or prophylactic agent for neuropathic pain, the agent comprising as effective ingredients a cyclohexane derivative represented by Formula (I) below:

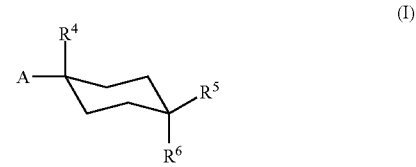

(I)

wherein A is a substituent represented by Formula (IIa) or (IIb):

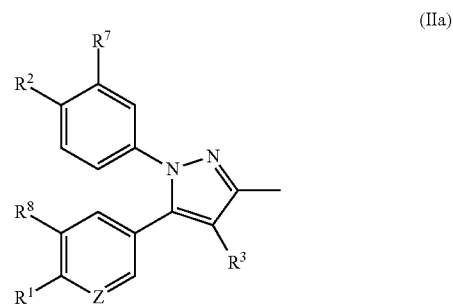

(IIa)

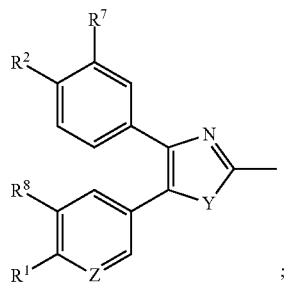

(IIb)

R¹ and R² are each independently a hydrogen atom, a chlorine atom, a $C_1$-$C_3$ haloalkyl group, a $C_1$-$C_4$ alkyl group or a $C_1$-$C_4$ alkoxy group; R³ is a hydrogen atom or a chlorine atom; R⁴ is a fluorine atom, a hydroxymethyl group or a hydroxyl group; R⁵ and R⁶ are each independently a hydrogen atom, a fluorine atom, a $C_1$-$C_3$ haloalkyl group, a carboxyl group, a methoxycarbonyl group, an ethoxycarbonyl group, a $C_1$-$C_4$ alkoxy group, a hydroxyl group or a $C_2$-$C_5$ alkylcarbonyloxy group, or optionally together form an oxo group; R⁷ and R⁸ are each independently a hydrogen atom or a fluorine atom; Y is an oxygen atom or a sulfur atom; and Z is a nitrogen atom or a methine group or a pharmaceutically acceptable salt thereof or a prodrug thereof, and a calcium channel α2δ ligand.

In the above-described cyclohexane derivative or a pharmaceutically acceptable salt thereof or a prodrug thereof, it is preferred that R¹ and R² be each independently a trifluoromethyl group, a methyl group or a methoxy group; R³ be a hydrogen atom; R⁴ be a hydroxymethyl group or a hydroxyl group; and R⁵ and R⁶ be each independently a hydrogen atom, a fluorine atom, a trifluoromethyl group, a carboxyl group, a methoxy group, a hydroxyl group or an acetyloxy group (or R⁵ and R⁶ may optionally together form an oxo group).

The above-mentioned calcium channel α2δ ligand is preferably pregabalin or gabapentin, more preferably pregabalin.

The therapeutic agent or the prophylactic agent for neuropathic pain can, while reducing the dose of the calcium channel α2δ ligand, synergistically enhance the analgesic effect which the calcium channel α2δ ligand has, and drastically reduce occurrence of the side effects on the central nervous system.

BRIEF DESCRIPTION OF THE DRAWINGS

FIG. 1 shows the effect of the combined use of Compound 3 and pregabalin in the mouse Seltzer model (changes over time at 1 hour, 2 hours and 3 hours after oral administration).

FIG. 2-A shows the effect of the combined use of Compound 3 and pregabalin in the mouse Seltzer model (at 1 hour after oral administration).

FIG. 2-B shows the effect of the combined use of Compound 3 and pregabalin in the mouse Seltzer model (at 2 hours after oral administration).

FIG. 3 shows the effect of the combined use of Compound 3 and pregabalin in the mouse wheel running test (from 0.5 to 1.5 hours after oral administration).

DETAILED DESCRIPTION

Figure 4:
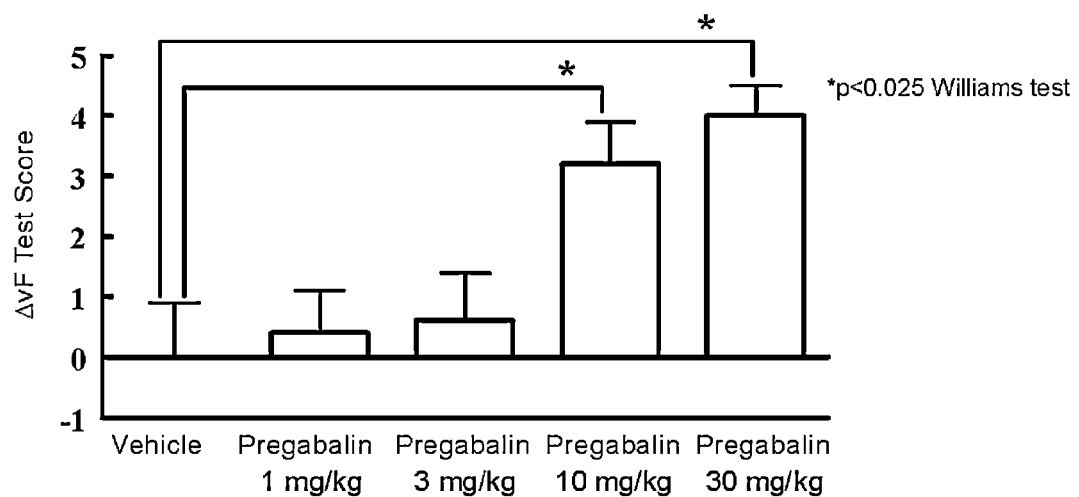
FIG. 4 shows the effect of the administration of pregabalin alone in the mouse Seltzer model (at 1 hour after oral administration).

The therapeutic agent or the prophylactic agent for neuropathic pain comprises as effective ingredients a cyclohexane derivative represented by Formula (I) below or a pharmaceutically acceptable salt thereof or a prodrug thereof, and a calcium channel α2δ ligand:

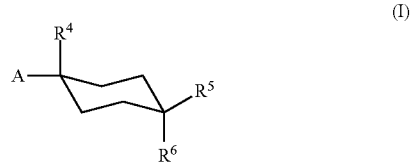

(I)

wherein A is a substituent represented by Formula (IIa) or (IIb):

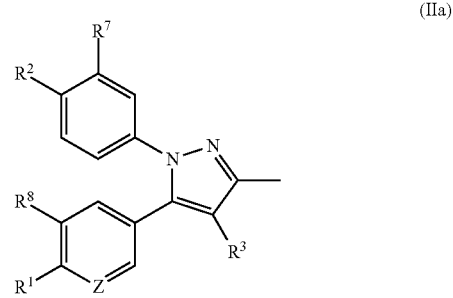

(IIa)

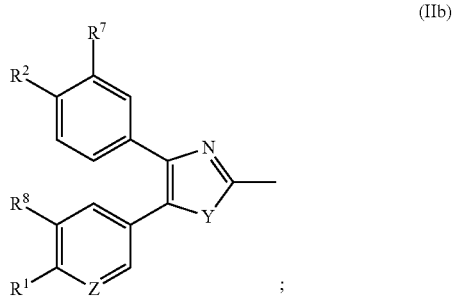

(IIb)

R¹ and R² are each independently a hydrogen atom, a chlorine atom, a $C_1$-$C_3$ haloalkyl group, a $C_1$-$C_4$ alkyl group or a $C_1$-$C_4$ alkoxy group; R³ is a hydrogen atom or a chlorine atom; R⁴ is a fluorine atom, a hydroxymethyl group or a hydroxyl group; R⁵ and R⁶ are each independently a hydrogen atom, a fluorine atom, a $C_1$-$C_3$ haloalkyl group, a carboxyl group, a methoxycarbonyl group, an ethoxycarbonyl group, a $C_1$-$C_4$ alkoxy group, a hydroxyl group or a $C_2$-$C_5$ alkylcarbonyloxy group, or R⁵ and R⁶ may optionally together form an oxo group; R⁷ and R⁸ are each independently a hydrogen atom or a fluorine atom; Y is an oxygen atom or a sulfur atom; and Z is a nitrogen atom or a methine group.

The term "$C_1$-$C_4$ alkyl group" means a linear, branched or cyclic alkyl group having 1 to 4 carbon atoms, and examples thereof include a methyl group, an ethyl group, an n-propyl group, an isopropyl group, a cyclopropyl group, a cyclopropylmethyl group, an n-butyl group, a sec-butyl group and a tert-butyl group.

The term "$C_1$-$C_4$ alkoxy group" means a linear, branched or cyclic alkyl-oxy group having 1 to 4 carbon atoms, and examples thereof include a methoxy group, an ethoxy group, an n-propyloxy group, an isopropyloxy group, a cyclopropyloxy group, an n-butoxy group, a sec-butoxy group and a tert-butoxy group.

The term "$C_1$-$C_3$ haloalkyl group" means a linear alkyl group having 1 to 3 carbon atoms wherein a part or all of the hydrogen atoms on the group are replaced by a halogen atom(s) (the halogen atom means a fluorine atom, a chlorine atom, a bromine atom or an iodine atom), and examples thereof include a monochloromethyl group, a monofluoromethyl group, a difluoro-methyl group, a trifluoromethyl group, a trichloromethyl group and a pentafluoroethyl group.

Examples of the "$C_2$-$C_5$ alkylcarbonyloxy group" include an acetyloxy group, an ethanoyloxy group, a propanoyloxy group, an isopropanoyloxy group, a butanoyloxy group, an isobutanoyloxy group and a pivaloyloxy group.

In Formula (I), A is preferably Formula (IIa); Y is preferably an oxygen atom; and Z is preferably a methine group.

$R^1$ is preferably a hydrogen atom, a chlorine atom, a trifluoromethyl group, a methyl group, an ethyl group, an n-propyl group, an isopropyl group, a methoxy group, an ethoxy group, an n-propyloxy group or an isopropyloxy group, more preferably a trifluoromethyl group, a methyl group or a methoxy group, and still more preferably a methyl group.

$R^2$ is preferably a hydrogen atom, a chlorine atom, a trifluoromethyl group, a methyl group, an ethyl group, an n-propyl group, an isopropyl group, a methoxy group, an ethoxy group, an n-propyloxy group or an isopropyloxy group, and more preferably a methoxy group.

$R^3$ is preferably a hydrogen atom; and $R^4$ is preferably a hydroxymethyl group or a hydroxyl group, and more preferably a hydroxyl group.

$R^5$ is preferably a hydrogen atom, a fluorine atom, a trifluoromethyl group, a carboxyl group, a methoxy group, an ethoxy group, an n-propyloxy group, an isopropyloxy group, a hydroxyl group, an acetyloxy group, a propanoyloxy group, a butanoyloxy group or an isobutanoyloxy group, more preferably a hydrogen atom, a hydroxyl group or a carboxyl group, and still more preferably a hydroxyl group.

$R^6$ is preferably a hydrogen atom, a fluorine atom, a trifluoromethyl group, a carboxyl group, a methoxy group, an ethoxy group, an n-propyloxy group, an isopropyloxy group, a hydroxyl group, an acetyloxy group, a propanoyloxy group, a butanoyloxy group or an isobutanoyloxy group, more preferably a hydrogen atom or a hydroxyl group, and still more preferably a hydrogen atom. $R^5$ and $R^6$ may optionally together form an oxo group.

$R^7$ and $R^8$ are each preferably a hydrogen atom.

Among cyclohexane derivatives represented by Formula (I) or pharmaceutically acceptable salts thereof or prodrugs thereof (hereinafter referred to as Compound (I)), preferred specific examples are shown in Table 1, but our therapeutic agents are not so limited.

TABLE 1

| Compound | Structural Formula |
|---|---|
| 1 | 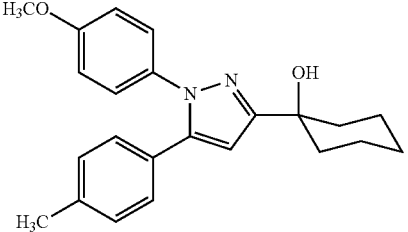 [SMILES: COc1ccc(-n2nc(C3(O)CCCCC3)cc2-c2ccc(C)cc2)cc1] |
| 2 | 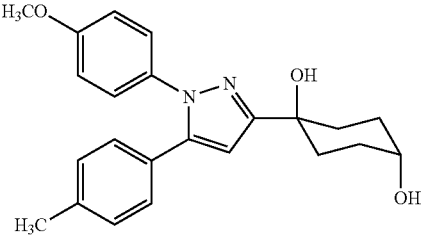 |
| 3 | 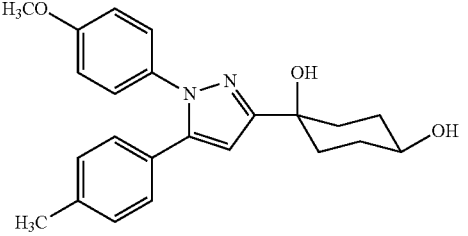 |

TABLE 1-continued
| Compound | Structural Formula |
|---|---|
| 4 | 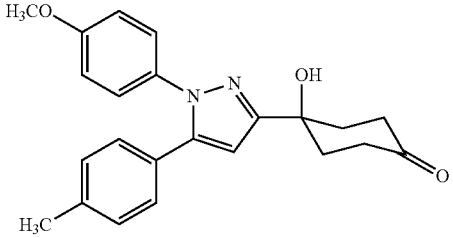 [SMILES: COc1ccc(-n2nc(C3(O)CCC(=O)CC3)cc2-c2ccc(C)cc2)cc1] |
| 5 | 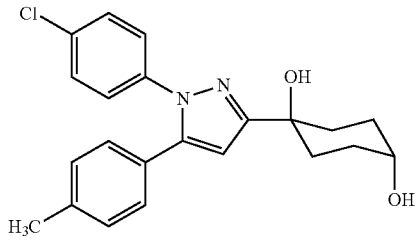 [SMILES: Cc1ccc(-c2cc(C3(O)CCC(O)CC3)nn2-c2ccc(Cl)cc2)cc1] |
| 6 | 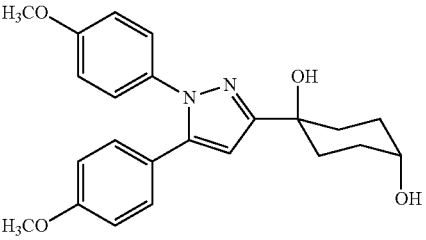 [SMILES: COc1ccc(-c2cc(C3(O)CCC(O)CC3)nn2-c2ccc(OC)cc2)cc1] |
| 7 | 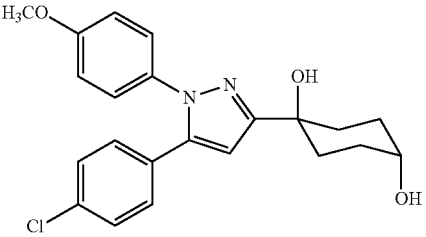 [SMILES: COc1ccc(-n2nc(C3(O)CCC(O)CC3)cc2-c2ccc(Cl)cc2)cc1] |
| 8 | 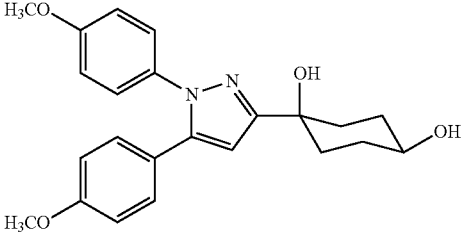 |
| 9 | 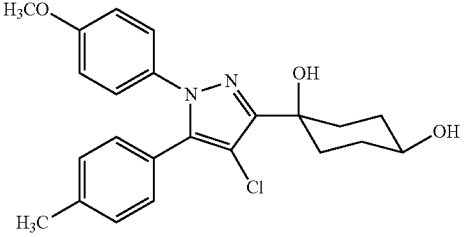 [SMILES: COc1ccc(-n2nc(C3(O)CCC(O)CC3)c(Cl)c2-c2ccc(C)cc2)cc1] |

TABLE 1-continued

| Compound | Structural Formula |
| --- | --- |
| 10 | |
| 11 | |
| 12 | |
| 13 | |
| 14 | |
| 15 | |

TABLE 1-continued

| Compound | Structural Formula |
| --- | --- |
| 16 | (4-methoxyphenyl / 4-methylphenyl pyrazole with 1-hydroxy-cyclohexane-CO₂H) |
| 17 | (4-methoxyphenyl / 4-methylphenyl pyrazole with 1-hydroxy-4,4-difluorocyclohexyl) |
| 18 | (4-methoxyphenyl / 4-trifluoromethylphenyl pyrazole with 1,4-dihydroxycyclohexyl) |
| 19 | (4-methoxyphenyl / 4-trifluoromethylphenyl pyrazole with 1,4-dihydroxycyclohexyl) |
| 20 | (4-methoxyphenyl / 4-methylphenyl pyrazole with 1-hydroxymethyl-4-hydroxycyclohexyl) |
| 21 | (4-methoxyphenyl / 4-chlorophenyl pyrazole with 1,4-dihydroxycyclohexyl) |

TABLE 1-continued

| Compound | Structural Formula |
| --- | --- |
| 22 | 1-(4-chlorophenyl)-5-(p-tolyl)pyrazol-3-yl cyclohexane-1,4-diol |
| 23 | 1,5-bis(4-chlorophenyl)pyrazol-3-yl cyclohexane-1,4-diol |
| 24 | 1,5-bis(4-chlorophenyl)pyrazol-3-yl cyclohexane-1,4-diol (isomer) |
| 25 | 5-(4-chlorophenyl)-1-phenylpyrazol-3-yl cyclohexane-1,4-diol |
| 26 | 5-(4-chlorophenyl)-1-phenylpyrazol-3-yl cyclohexane-1,4-diol (isomer) |
| 27 | 1,5-bis(p-tolyl)pyrazol-3-yl cyclohexane-1,4-diol |

TABLE 1-continued
| Compound | Structural Formula |
|---|---|
| 28 | 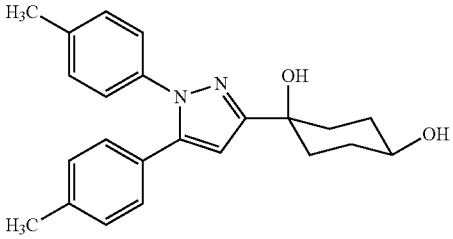 |
| 29 | 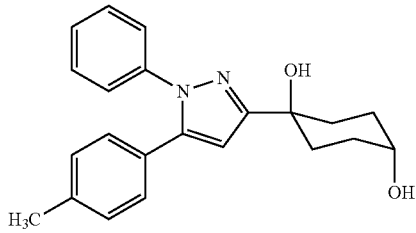 [SMILES: Cc1ccc(-c2cc(C3(O)CCC(O)CC3)nn2-c2ccccc2)cc1] |
| 30 | 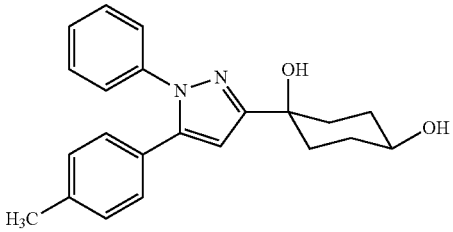 [SMILES: Cc1ccc(-c2cc(C3(O)CCC(O)CC3)nn2-c2ccccc2)cc1] |
| 31 | 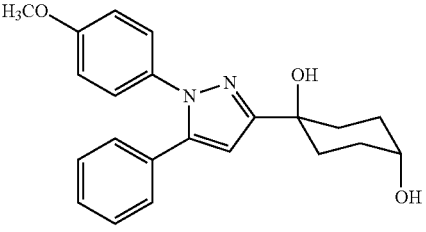 [SMILES: COc1ccc(-n2nc(C3(O)CCC(O)CC3)cc2-c2ccccc2)cc1] |
| 32 | 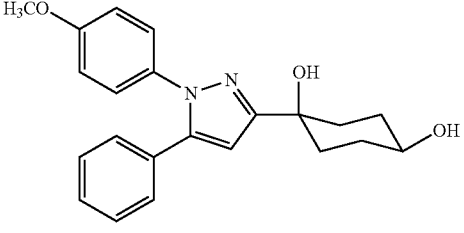 [SMILES: COc1ccc(-n2nc(C3(O)CCC(O)CC3)cc2-c2ccccc2)cc1] |
| 33 | 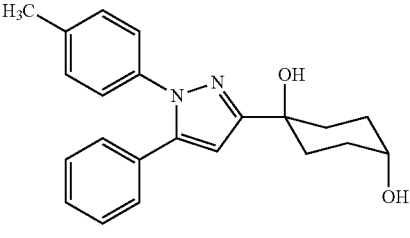 [SMILES: Cc1ccc(-n2nc(C3(O)CCC(O)CC3)cc2-c2ccccc2)cc1] |

TABLE 1-continued

| Compound | Structural Formula |
|---|---|
| 34 | |
| 35 | |
| 36 | |
| 37 | |
| 38 | |
| 39 | |

TABLE 1-continued

| Compound | Structural Formula |
|---|---|
| 40 | |
| 41 | |
| 42 | |
| 43 | |
| 44 | |
| 45 | |

TABLE 1-continued
| Compound | Structural Formula |
|---|---|
| 46 | 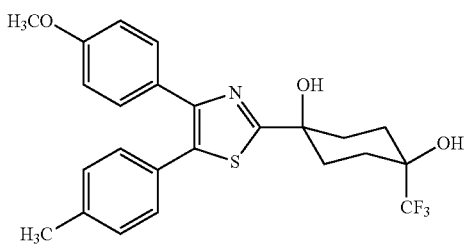 [SMILES: COc1ccc(-c2nc(C3(O)CCC(O)(C(F)(F)F)CC3)sc2-c2ccc(C)cc2)cc1] |
| 47 | 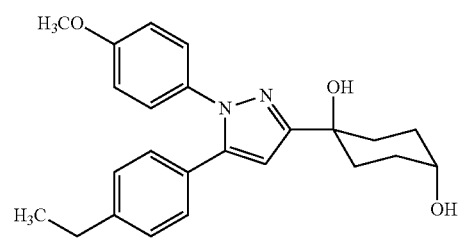 [SMILES: CCc1ccc(-c2cc(C3(O)CCC(O)CC3)nn2-c2ccc(OC)cc2)cc1] |
| 48 | 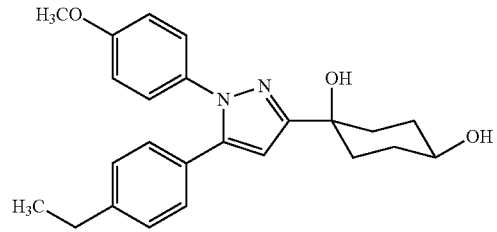 [SMILES: CCc1ccc(-c2cc(C3(O)CCC(O)CC3)nn2-c2ccc(OC)cc2)cc1] |
| 49 | 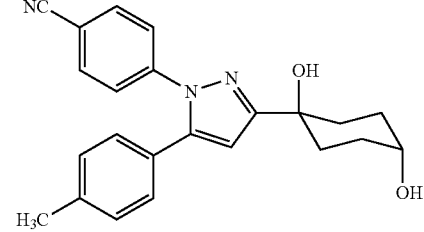 [SMILES: Cc1ccc(-c2cc(C3(O)CCC(O)CC3)nn2-c2ccc(C#N)cc2)cc1] |
| 50 | 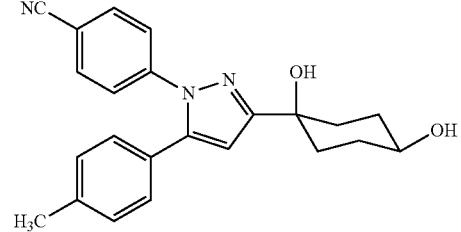 [SMILES: Cc1ccc(-c2cc(C3(O)CCC(O)CC3)nn2-c2ccc(C#N)cc2)cc1] |
| 51 | 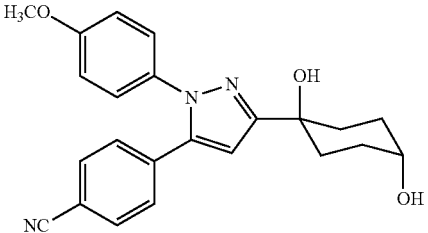 [SMILES: COc1ccc(-n2nc(C3(O)CCC(O)CC3)cc2-c2ccc(C#N)cc2)cc1] |

TABLE 1-continued

| Compound | Structural Formula |
|---|---|
| 52 | |
| 53 | |
| 54 | |
| 55 | |
| 56 | |

TABLE 1-continued

| Compound | Structural Formula |
|---|---|
| 57 | (4-methoxyphenyl/4-methylphenyl pyrazole)-C(OH)(cyclohexyl-CO₂CH₃) |
| 58 | (4-methoxyphenyl/4-methylphenyl pyrazole)-C(OH)(cyclohexyl-CO₂Et) |
| 59 | (4-methoxyphenyl/4-methylphenyl pyrazole)-C(OH)(cyclohexyl-O-C(O)-N(CH₃)₂) |
| 60 | (4-methoxyphenyl/4-methylphenyl pyrazole)-C(OH)(cyclohexyl-O-C(O)-O-cyclohexyl) |
| 61 | (4-methoxyphenyl/4-methylphenyl pyrazole)-C(OH)(cyclohexyl-O-C(O)-OCH₂CH₃) |

TABLE 1-continued

| Compound | Structural Formula |
|---|---|
| 62 | |
| 63 | |
| 64 | |
| 65 | |
| 66 | |

TABLE 1-continued

| Compound | Structural Formula |
|---|---|
| 67 | *(structure: 1-(4-methoxyphenyl)-5-(4-methylphenyl)pyrazol-3-yl attached to a 1-hydroxycyclohexyl group esterified with glycine)* |
| 68 | *(structure: same pyrazolyl-hydroxycyclohexyl core, esterified with valine)* |
| 69 | *(structure: same pyrazolyl-hydroxycyclohexyl core, with —O—CH₂—O—C(=O)—CH(NH₂)—CH(CH₃)₂ substituent)* |
| 70 | *(structure: same pyrazolyl-hydroxycyclohexyl core, with —O—P(=O)(OH)₂ phosphate substituent)* |

Compound (I) includes all the enantiomers and mixtures thereof in cases where Compound (I) has an asymmetric carbon(s).

Compound (I) includes all the stereoisomers and mixtures thereof in cases where Compound (I) has a stereoisomer(s).

Examples of the calcium channel α2δ ligand to be used in combination with Compound (I) include pregabalin (S-(+)-4-amino-3-(2-methylpropyl) butanoic acid or (S)-3-(aminomethyl)-5-(methylhexanoic acid)) and gabapentin (1-(aminomethyl)-cyclohexaneacetic acid or 2-[1-(aminomethyl)cyclohexane]acetic acid), and pharmaceutically acceptable salts thereof and prodrugs thereof. Pregabalin or gabapentin is preferred, and pregabalin is more preferred.

Examples of the "pharmaceutically acceptable salt" include inorganic acid salts such as hydrochloric acid salt, sulfuric acid salt, phosphoric acid salt and hydrobromic acid salt; organic acid salts such as oxalic acid salt, malonic acid salt, citric acid salt, fumaric acid salt, lactic acid salt, malic acid salt, succinic acid salt, tartaric acid salt, acetic acid salt, trifluoroacetic acid salt, maleic acid salt, gluconic acid salt, benzoic acid salt, ascorbic acid salt, methane-sulfonic acid salt, p-toluenesulfonic acid salt and cinnamic acid salt; inorganic base salts such as sodium salt, potassium salt, calcium salt, magnesium salt and ammonium salt; and organic base salts such as methylamine salt, diethylamine salt, trimethylamine salt, triethylamine salt, pyridinium salt, triethanolamine salt, ethylenediamine salt and guanidine salt. Further, Compound (I) may form a hydrate or a solvate, and crystalline polymorphs are also included therein.

Compound (I) may be synthesized, for example, according to a method as described in WO 10/050577.

The calcium channel α2δ ligand may be synthesized, for example, according to a method as described in JP 51-88940 A, JP 7-508288 A or JP 2004-536873 A.

A therapeutic agent or a prophylactic agent for neuropathic pain which comprises as effective ingredients Compound (I) and a calcium channel α2δ ligand also exhibits an excellent analgesic effect when administered to a mammal other than humans. Examples of mammals other than humans include mice, rats, hamsters, rabbits, cats, dogs, bovines, sheep and monkeys.

Examples of the "neuropathic pain" include cancer pain, herpetic pain, postherpetic neuralgia, AIDS-related neuralgia, trigeminal neuralgia and diabetic neuropathic pain.

As for a mode of administration of a therapeutic agent or a prophylactic agent for neuropathic pain which comprises as effective ingredients Compound (I) and a calcium channel α2δ ligand, a mixture of both ingredients, i.e., a combination drug of both may be administered orally or parenterally as it is or after further combining it with a carrier which is acceptable as a pharmaceutical. Alternatively, Compound (I) and a calcium channel α2δ ligand may be individually prepared as single drugs, not as a combination drug, and then these may be administered at the same time as they are or after further combining each of them with a carrier which is acceptable as a pharmaceutical. Furthermore, the individual single drugs may also be administered such that either one of the single drugs is administered after the other at an appropriate interval. In these cases, the dosage forms and the administration routes of the individual single drugs do not need to be same, and may be different from each other. The "appropriate interval" as mentioned above may be confirmed clinically or by animal experiments.

Examples of the dosage form in cases where Compound (I) and a calcium channel α2δ ligand are orally administered as individual single drugs or as a combination drug include tablets (including sugar coated tablets and film coated tablets), pills, granules, powders, capsules (including soft capsules and microcapsules), syrups, emulsions and suspensions; and examples of the dosage form in cases where they are parenterally administered include injection solutions, impregnating agents, drops and suppositories. Furthermore, it is also effective to combine the effective ingredient(s) with an appropriate base (for example, a polymer of butyric acid, a polymer of glycolic acid, a copolymer of butyric acid-glycolic acid, a mixture of a polymer of butyric acid and a polymer of glycolic acid, a polyglycerol fatty acid ester or the like) to form a sustained release formulation(s).

Preparation of single drugs or a combination drug of Compound (I) and a calcium channel α2δ ligand in the above-mentioned dosage form may be carried out according to known production methods commonly used in the field of formulation of pharmaceuticals. In this case, the drugs may be produced such that an excipient, a binder, a lubricant, a disintegrator, a sweetener, a surfactant, a suspending agent, an emulsifier and/or the like which is(are) commonly used in the field of formulation of pharmaceuticals is(are) contained therein as required.

Single drugs or a combination drug of Compound (I) and a calcium channel α2δ ligand may be prepared in the form of tablets such that an excipient, a binder, a disintegrator, a lubricant and/or the like is(are) contained therein; or in the form of pills or granules such that an excipient, a binder, a disintegrator and/or the like is(are) contained therein. In addition, the single drugs or the combination drug may be prepared in the form of powders or capsules such that an excipient and/or the like is contained therein; in the form of syrups such that a sweetener and/or the like is contained therein; or in the form of emulsions or suspensions such that a surfactant, a suspending agent, an emulsifier and/or the like is(are) contained therein.

Examples of the above-mentioned excipient include lactose, glucose, starch, sucrose, microcrystalline cellulose, powdered glycyrrhiza, mannitol, sodium hydrogen carbonate, calcium phosphate and calcium sulfate.

Examples of the above-mentioned binder include a starch paste solution, a gum arabic solution, a gelatin solution, a tragacanth solution, a carboxymethylcellulose solution, a sodium alginate solution and glycerin.

Examples of the above-mentioned disintegrator include starch and calcium carbonate.

Examples of the above-mentioned lubricant include magnesium stearate, stearic acid, calcium stearate and purified talc.

Examples of the above-mentioned sweetener include glucose, fructose, invert sugar, sorbitol, xylitol, glycerin and simple syrup.

Examples of the above-mentioned surfactant include sodium lauryl sulfate, polysorbate 80, sorbitan monofatty acid ester and polyoxyl 40 stearate.

Examples of the above-mentioned suspending agent include gum arabic, sodium alginate, sodium carboxymethylcellulose, methylcellulose and bentonite.

Examples of the above-mentioned emulsifier include gum arabic, tragacanth, gelatin and polysorbate 80.

In addition, in the preparation of single drugs or a combination drug of Compound (I) and a calcium channel α2δ ligand in the above-mentioned dosage form, a colorant, a preservative, an aromatic, a corrigent, a stabilizer, a thickener and/or the like which is(are) commonly used in the field of formulation of pharmaceuticals may be added therein.

The daily dose of the formulation which comprises a calcium channel α2δ ligand varies depending on the conditions and the body weight of the patient, the type of the inhibitor, the administration route and/or the like. For example, in cases where gabapentin is orally administered, it is preferred that administration be carried out at an amount of 10 to 3600 mg per adult (body weight: about 60 kg), once or up to three times dividedly; and in cases where pregabalin is orally administered, it is preferred that administration be carried out at an amount of 5 to 600 mg per adult (body weight: about 60 kg), once or up to three times dividedly. With regard to the daily dose of the formulation which comprises Compound (I), for example, in cases where the formulation is orally administered, it is preferred that administration be carried out at an amount of 1 to 1000 mg per adult (body weight: about 60 kg), once or up to three times dividedly; and, in cases where the formulation is parenterally administered, it is preferred that, if the formulation is injection solution, administration be carried out at an amount of 0.01 to 100 mg per 1 kg of body weight by intravenous injection.

EXAMPLES

Our therapeutic agents will now be described more concretely by way of an example thereof. However, this disclosure is not restricted to the example below.

Example 1

Combined Effect of Compound (I) and Calcium Channel α2δ Ligand in Mouse Neuropathic Pain Model For the evaluation, 7 to 8 male ICR mice of 5 weeks old were used for one experimental group. Mouse models of neuropathic pain were prepared according to Seltzer's method (Seltzer et al., Pain, 1990, vol. 43, p. 205; Malmberg et al., Pain, 1998, vol. 76, p. 215). That is, the sciatic nerve at the femoral region of the right hindlimb of each mouse was exposed under anesthesia, and the sciatic nerve was triply ligated tightly with silk suture of 8-0 (NATSUME SEISAKUSHO) under microscope so that only half thickness of the nerve was trapped in the ligature.

As a test compound, 1-(1-(4-methoxyphenyl)-5-(p-tolyl)-1H-pyrazol-3-yl)cyclohexan-cis-1,4-diol (hereinafter referred to as Compound 3), which was represented by the following formula and included in Compound (I), was selected.

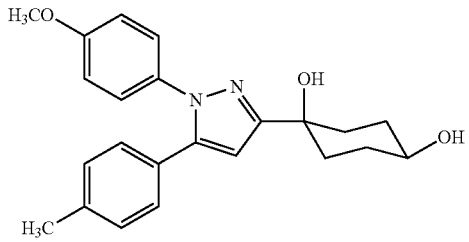

As a calcium channel α2δ ligand, pregabalin was selected.

The mouse models of neuropathic pain were splitted into 4 groups; a group treated with vehicle (Vehicle in FIG. 1 and FIG. 2), a group treated with 3 mg/kg pregabalin alone (Pregabalin in FIG. 1 and FIG. 2), a group treated with 0.3 mg/kg Compound 3 alone (Compound 3 in FIG. 1 and FIG. 2), and a group concomitantly treated with 3 mg/kg pregabalin and 0.3 mg/kg Compound 3 (Pregabalin+Compound 3 in FIG. 1 and FIG. 2).

Seven days after the above-described sciatic nerve ligation, using 0.5% methylcellulose as a vehicle, mice of each group received administration of vehicle, administration of a suspension of pregabalin (3 mg/kg) alone, administration of a suspension of Compound 3 (0.3 mg/kg) alone, or administration (combined administration) of a mixed suspension of pregabalin and Compound 3 (3 mg/kg and 0.3 mg/kg, respectively).

Evaluation of neuropathic pain (hereinafter "von Frey test") was carried out as follows. Mouse models of neuropathic pain were conditioned for at least 1 hour in an acryl cage for measurement (NATSUME SEISAKUSHO) placed on a wire net. Thereafter, using a filament (North Coast Medical. Inc.) which exerted a pressure of 0.16 g, the mice were subjected to mechanical tactile stimulus by applying the filament to the plantar surface of both hindpaws 3 times, each for 3 seconds, with an interval of 3 seconds. The withdrawal response observed during each mechanical tactile stimulus was scored (0, no response; 1, showed slow and/or slight withdrawal response in response to the stimulation; 2, showed quick withdrawal response without flinching (shaking paws quickly and continuously) nor licking (licking paws) in response to the stimulation; 3, showed quick withdrawal response with flinching and/or licking), and the sum of the scores obtained in the triplicate trials were used as a total score.

Seven days after sciatic nerve ligation, a von Frey test was carried out before administration of the test compound, 1 hour after administration, 2 hours after administration, and 3 hours after administration. Change in the total scores from before to after administration of the test compound (hereinafter "ΔvF test score") was calculated by subtracting the total score obtained at each time point after administration of the test compound from the total score obtained before administration of the test compound, which was used as an indicator of analgesic effect.

A theoretical total value, which was the theoretical ΔvF test score calculated on the assumption that combined use of Compound 3 and pregabalin exhibited no more than an additive analgesic effect, was calculated based on the ΔvF test scores obtained when Compound 3 or pregabalin was administered alone. That is, individual ΔvF test scores of the mice in the group treated with pregabalin alone and the mice in the group treated with Compound 3 alone were sorted in ascending order, respectively, and ΔvF test scores of the two groups at the same rank were added, thereby obtaining a theoretical total value.

Results of the evaluation are shown in FIG. 1, FIG. 2-A and FIG. 2-B. In the figures, the vertical axis shows the ΔvF test score of the von Frey test, and a higher score indicates a stronger analgesic effect. The horizontal axis of FIG. 1 shows time after administration of the test compound, and that of FIG. 2 shows how each group was treated.

Statistical comparison between the group treated with vehicle and the groups treated with drugs at each time point was carried out using Dunnett's test since interactions between group and time were found to be significant by two-way ANOVA (with a level of significance of less than 5%). The symbol # in the figures indicates a significant difference (###$p<0.001$) from the group treated with vehicle. Statistical comparison between the group concomitantly treated with 3 mg/kg pregabalin and 0.3 mg/kg Compound 3 (Pregabalin+Compound 3 in FIG. 2) and the theoretical total value was carried out using Student's t-test since variances were found to be equal by F-test (with a level of significance of less than 5%). The symbol * in the figures indicates a significant difference (*$p<0.05$, **$p<0.01$) from the theoretical total value.

In the group treated with 3 mg/kg pregabalin alone (Pregabalin in FIG. 1 and FIG. 2), an analgesic effect was not observed at any time points of 1 hour, 2 hours and 3 hours after administration. Also in the group treated with 0.3 mg/kg Compound 3 alone (Compound 3 in FIG. 1 and FIG. 2), an analgesic effect was not observed at any time points of 1 hour, 2 hours and 3 hours after administration.

On the other hand, in the concomitant treatment group (Pregabalin+Compound 3 in FIG. 1 and FIG. 2), a strong analgesic effect was observed 1 hour and 2 hours after administration with a statistical significance when compared to the vehicle treatment group (Vehicle in FIG. 1 and FIG. 2). Furthermore, a statistically significant difference was found between the theoretical total value (Theoretical Total Value in FIG. 2) and the concomitant treatment group (Pregabalin+Compound 3 in FIG. 2) at time points of both 1 hour and 2 hours after administration. These results clearly indicate that Compound (I) and a calcium channel α2δ ligand synergistically enhance their analgesic effects each other when used in combination.

Example 2

Combined Effect of Compound (I) and Calcium Channel α2δ Ligand in Mouse Wheel Running Test For the evaluation, 8 male ddY mice of 5 weeks old were used for one experimental group. The test compound, grouping of mice, vehicle used and administration method were the same as in Example 1.

Mice were placed in a running wheel apparatus (NATSUME SEISAKUSHO) 0.5 hour after administration of the test compound, and the number of revolutions of the running wheel was counted for a period of 1 hour immediately thereafter to evaluate a motor inhibitory effect.

Results of the evaluation are shown in FIG. 3. The vertical axis shows the number of revolutions in the wheel running test. A higher value indicates that mice are more physically-active. The horizontal axis shows how each group was treated.

Statistical comparison between the vehicle treatment group (Vehicle in FIG. 3) and the drug treatment groups was carried out using Student's t-test since variances were found to be equal by F-test (with a level of significance of less than 5%).

No statistically-significant motor inhibitory effect was found in the group treated with 3 mg/kg pregabalin alone (Pregabalin in FIG. 3) and in the group treated with 0.3 mg/kg Compound 3 alone (Compound 3 in FIG. 3). Further, no statistically-significant motor inhibitory effect was found also in the group concomitantly treated with 3 mg/kg pregabalin and 0.3 mg/kg Compound 3 (Pregabalin+Compound 3 in FIG. 3). These results clearly indicate that the central nervous system does not adversely affected by combined use of Compound (I) and a calcium channel α2δ ligand each in a dose not adversely affecting the central nervous system.

Comparative Example 1

Effect of Calcium Channel α2δ Ligand in Mouse Models of Neuropathic Pain

In the same manner as in Example 1, effects of oral administration of 1, 3, 10 and 30 mg/kg pregabalin alone were evaluated 1 hour after administration in mouse models of neuropathic pain.

Results of evaluation are shown in FIG. 4. Statistical comparison between the group treated with vehicle (Vehicle in FIG. 4) and the groups treated with pregabalin (Pregabalin 1 mg/kg, Pregabalin 3 mg/kg, Pregabalin 10 mg/kg and Pregabalin 30 mg/kg in FIG. 4) was carried out using a Williams test (one-way) since variances were found to be equal by a Bartlett test (with a level of significance of less than 5%). The symbol * in the figure indicates a significant difference (*p<0.025) from the group treated with vehicle.

No analgesic effect was observed when 1 or 3 mg/kg of pregabalin was orally administered alone. On the other hand, a statistically-significant analgesic effect was observed when 10 or 30 mg/kg of pregabalin was orally administered alone. In addition, it was thought that the analgesic effect of 30 mg/kg pregabalin was about the same level as that of the combined administration of 3 mg/kg pregabalin and 0.3 mg/kg Compound 3.

Comparative Example 2

Effect of Calcium Channel α2δ Ligand in Mouse Wheel Running Test

In the same manner as in Example 2, motor inhibitory effects of oral administration of 30 and 100 mg/kg pregabalin were evaluated.

Figure 5:
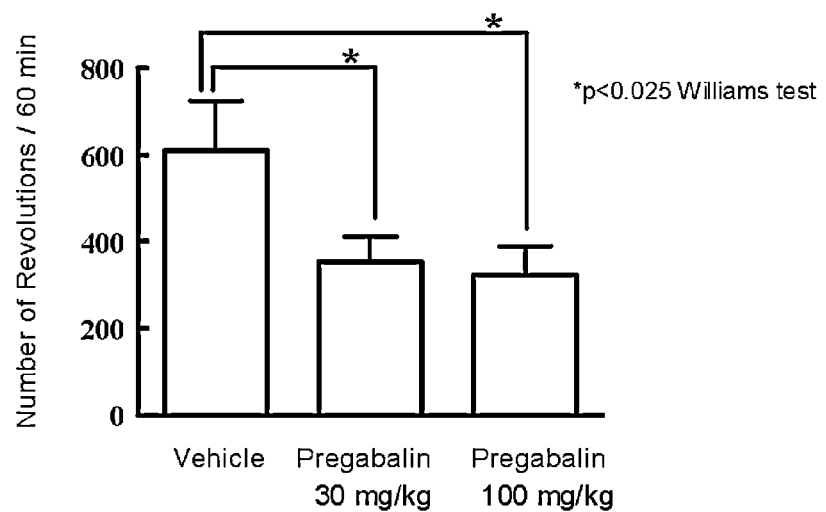
FIG. 5 shows the effect of the administration of pregabalin alone in the mouse wheel running test (from 0.5 to 1.5 hours after oral administration).

Results of evaluation are shown in FIG. 5. Statistical comparison between the group treated with vehicle (Vehicle in FIG. 5) and the groups treated with 30 and 100 mg/kg pregabalin (Pregabalin 30 mg/kg and Pregabalin 100 mg/kg in FIG. 5, respectively) was carried out using a Williams test (one-way) since variances were found to be equal by a Bartlett test (with a level of significance of less than 5%). The symbol * in the figure indicates a significant difference (*p<0.025) from the group treated with vehicle.

Oral administration of 30 or 100 mg/kg pregabalin alone statistically significantly reduced the number of revolutions, thereby confirming a motor inhibitory effect.

INDUSTRIAL APPLICABILITY

Our agents include as effective ingredients Compound (I) and a calcium channel α2δ ligand, and can be used as a pharmaceutical, especially as a therapeutic agent or a prophylactic agent for neuropathic pain.

The invention claimed is:

1. A therapeutic agent for the treatment of neuropathic pain comprising as effective ingredients a cyclohexane derivative represented by Formula (I):

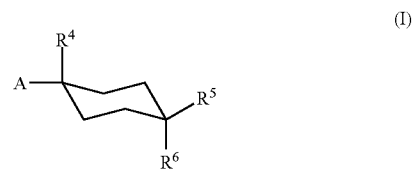

wherein
A is a substituent represented by Formula (IIa):

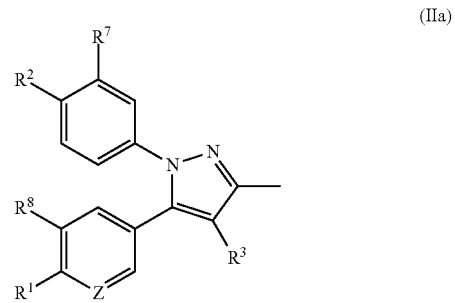

wherein $R^1$ and $R^2$ are each independently a $C_1$-$C_4$ alkyl group or a $C_1$-$C_4$ alkoxy group;
$R^3$ is a hydrogen atom; $R^4$ is a hydroxyl group;
$R^5$ and $R^6$ are each independently a hydrogen atom, or a hydroxyl group;
$R^7$ and $R^8$ are a hydrogen atom;
Z is a methine group
or a pharmaceutically acceptable salt thereof and a calcium channel α2δ ligand which is pregabalin or gabapentin.

2. The therapeutic agent according to claim 1, wherein $R^1$ and $R^2$ are each independently a methyl group or a methoxy group.

3. The therapeutic agent according to claim 1, wherein $R^1$ is a methyl group, $R^2$ is a methoxy group, $R^5$ is a hydroxyl group, and $R^6$ is a hydrogen atom.

* * * * *